United States Patent [19]

Siemion

[11] Patent Number: 4,483,374
[45] Date of Patent: Nov. 20, 1984

[54] CHROMATOGRAPHIC COLUMN

[75] Inventor: Chester C. Siemion, Sterling Heights, Mich.

[73] Assignee: Ethyl Corporation, Richmond, Va.

[21] Appl. No.: 438,171

[22] Filed: Nov. 1, 1982

[51] Int. Cl.³ .............................................. B65B 3/04
[52] U.S. Cl. ......................................... 141/9; 141/12; 210/656
[58] Field of Search ..................................... 141/1–12; 73/61.1 C, 23.1; 422/89, 256, 41; 210/635, 656, 657, 658, 659

[56] References Cited
U.S. PATENT DOCUMENTS
3,080,746 3/1963 Nerheim .......................... 73/61.1 C Primary Examiner—Houston S. Bell, Jr.
Attorney, Agent, or Firm—Donald L. Johnson; John F. Sieberth; Joseph D. Odenweller

[57] ABSTRACT

A method is provided for packing a high pressure liquid chromatographic column to obtain increased efficiency by suspending the packing in an alcohol medium between a lower liquid phase (e.g. carbon tetrachloride) and an upper liquid phase (e.g. isooctane) and passing the liquids under high pressure through an unpacked column lower layer first. The packing is retained in the column.

6 Claims, 1 Drawing Figure

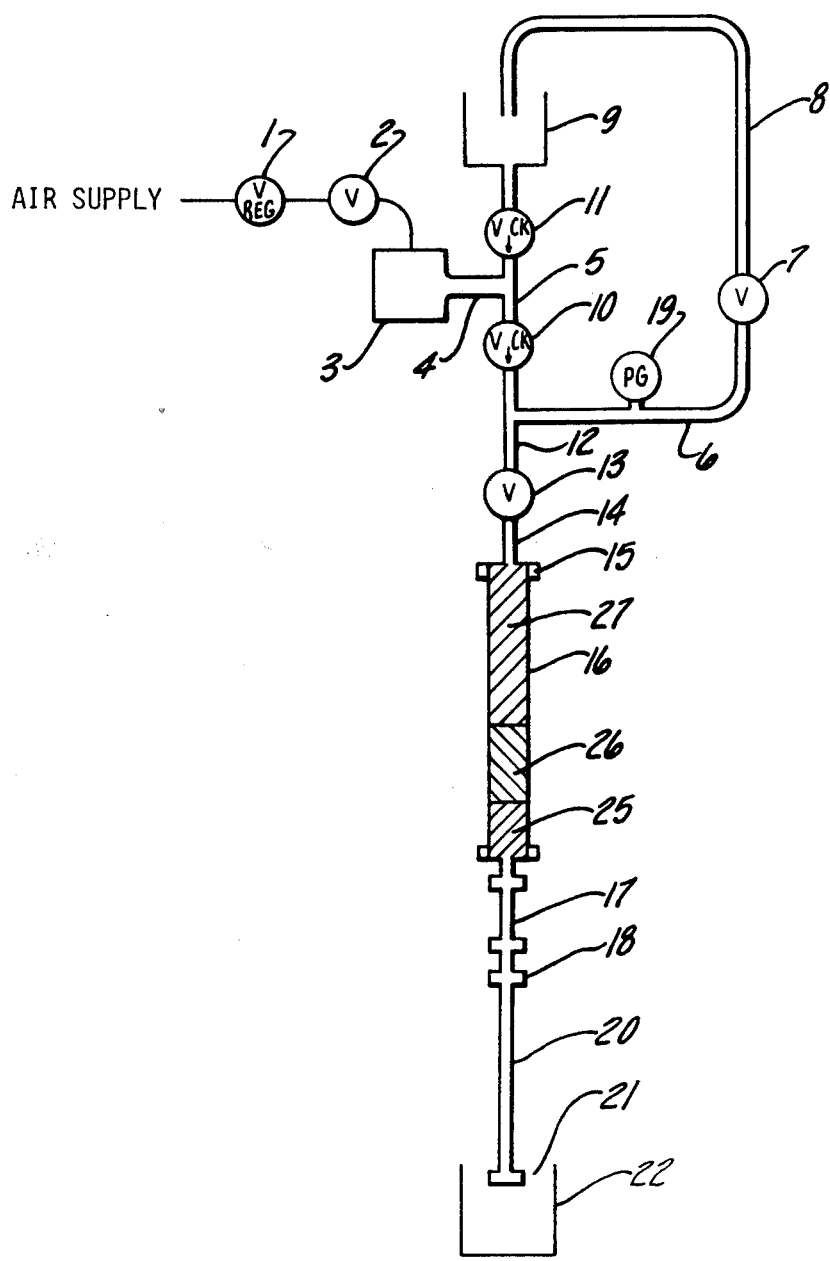

CHROMATOGRAPHIC COLUMN

BACKGROUND

Methods and equipment for packing of high pressure liquid chromatographic (HPLC) columns have been described, E. J. Kikta, *Journal of Liquid Chromatography*, 2, p. 129 (1979); G. E. Bernendsen et al, Anal. Chem. 51, 1091 (1979).

Initial attempts at column packing utilized the generally recommended techniques of filling the column with isopropanol, adding a slurry of packing in isopropanol, pressurizing and packing with isooctane. These produced usable columns, but they were rather low in plate count (10,000 to 12,000 plates per meter).

SUMMARY

It has now been discovered that a superior high efficiency (HPLC) column can be made by suspending the packing material in alcohol as a "slug" between a lower high-density liquid annd an upper low-density liquid and rapidly injecting the three-liquid system through an unpacked column, lower liquid first. The liquids pass through while the packing is retained by a porous frit.

DESCRIPTION OF THE DRAWING

The drawing is a not-to-scale view of an apparatus for carrying out the process.

DESCRIPTION OF THE PREFERRED EMBODIMENTS

A preferred embodiment of the invention is a method for packing a high pressure liquid chromatographic column to obtain increased efficiency, said method comprising (a) suspending a column packing material in an alcohol medium to obtain a liquid packing suspension, said alcohol having a density similar to the density of said packing material. (b) forming a packing fluid comprising a lower liquid phase, a middle liquid phase and an upper liquid phase, said lower liquid phase having a density greater than said middle liquid phase, said middle liquid phase consisting of said liquid packing suspension, said upper liquid phase being an inert liquid having a density lower than said middle liquid phase, (c) rapidly injecting said packing fluid downwardly under high pressure into the inlet of an unpacked chromatographic column having an inlet and an outlet end, said column having retainer means at said outlet end which retain said packing material in said chromatographic column and permit liquids to pass through.

The lower liquid phase can be any liquid which is more dense than the middle liquid alcohol phase and substantially inert to the middle alcohol phase. It need not be completely immiscible with the middle alcohol phase as long as it does not readily dissolve in the alcohol and can maintain a distinct lower liquid phase during the short time needed to complete the process.

Preferred lower liquid phase materials are the halogenated hydrocarbons such as carbon tetrachloride, 1,2-chlorobromoethane, 1,1,1-chlorodibromoethane, 1,1,2-chlorodibromomethane, chlorodibromomethane, trichloromethane, dichloromethane, 1,1-dibromomethane, 1,2-dibromoethane, 1,2-dibromohexane, 1,6-dibromohexane, 3,4-dibromo-2,2-dimethylbutane, and the like. The most preferred lower liquid phase is carbon tetrachloride.

The amount of lower liquid phase is not critical as long as there is a sufficient amount to fill the unpacked chromatographic column.

The middle liquid phase should be a polar compound or mixture of compounds which can maintain the particular column packing in suspension for at least the short period of time required to complete the process. Alcohols are effective in this function, especially if they are selected or blended to have a density close to that of the packing. Suitable alcohols include methanol (d 0.79), ethanol (d. .789), n-propanol (d.804), isopropanol (d .785), n-butanol (d .810), isobutanol (d .808), and the like. Equivalent results have not been obtained with every alcohol and packing combination. With silica packing, excellent results have been obtained using isopropanol which is the most preferred middle liquid phase.

The amount of middle liquid phase should be an amount which will maintain the required amount of packing material in suspension. Only a few grams of packing are required to fill a 25 cm. HPLC chromatographic column. This can readily be slurried in about 25 ml. alcohol.

The upper liquid phase can be any inert liquid which has a density less than the middle liquid phase. It should not readily dissolve into the middle liquid phase during the few minutes it takes to complete the process. The preferred upper liquid phase is an aliphatic liquid hydrocarbon boiling in the range of about 50°–200° C. These include n-octane (d 0.703), 2,2,3-trimethylpentane (d .716), 2,2,4-trimethylpentane (d .692), 2,4-dimethylhexane (d .700), 2-methylheptane (d .698), n-hexane (d .659), 2-methyl pentane (d .654), 2,2-dimethyl butane (d .649), n-heptane (d .684), 2-methyl hexane (d .679), n-decane (d .730) and the like, including mixtures thereof.

Excellent results have been obtained using isooctane.

The amount of upper liquid phase should be enough to fill the reservoir.

The method of conducting the process is best understood by reference to the drawing. The drawing is a not-to-scale diagram of an apparatus especially adapted to pack HPLC columns according to the present process.

The apparatus comprises an air pressure supply which delivers air through pressure regulating valve 1, main air valve 2 to air driven pressure amplification pump 3, (Haskel DSTV 122C). This pump is a reciprocating type liquid pump which connects through conduit 4 to conduit 5 which connects through one-way check valve 10 to conduit 6 through valve 7 and conduit 8 to discharge into open tank 9. The bottom of tank 9 connects through one-way check valve 11 back to conduit 5 forming a loop.

Conduit 12 connects the loop through valve 13, conduit 14 and coupling 15 to the top of reservoir 16. The bottom of reservoir 16 connects through pre-column 17 and coupling 18 to an empty chromatographic column 20 (4.6 mm. i.d.×25 cm. L stainless steel). At the bottom discharge end of column 20 is attached end fitting 21 which includes a 2 micron internal frit to retain packing. Bucket 22 is placed below the discharge end of column 20 to catch the liquid discharged under high pressure.

In operation tank 9 is filled with isooctane which will be the upper liquid phase in the three-phase system. Valve 7 is then opened slightly and the air supply is adjusted to about 20 psig. by regulator valve 1. Valve 2 is then opened, actuating pump 3 to alternatively deliver pressure and suction to conduit 5. On suction, isooctane is drawn down from tank 9 through one-way check valve 11 and on the pressure cycle the isooctane is forced through one-way check valve 10 and conduits 6 and 8 to discharge back into tank 9. This is continued until the system is filled with isooctane. Then valve 7 is closed and the regulator valve 1 is adjusted until pressure gauge 19 reads 10,000 psig. Valve 2 is then closed to inactivate pump 3 and valve 7 is opened to relieve the pressure in the loop. Note that regulator valve 1 is still set to deliver the air pressure required (approximately 85 psig.) to cause pump 3 to pump isooctane in conduit 5 back to 10,000 psig. when valve 2 is later opened.

The packing material (e.g. 2.9 g. 10 micron spherical silica "Spherisorb S10W" available from Alltech Association, Inc., Deerfield, Illinois) is then slurried in 25 ml. isopropanol in a 50 ml. flask. This is placed under vacuum and sonicated with a high frequency sound for about one minute to de-gas the silica and isopropanol. Reservoir 16 is disconnected at coupling 15 and 25 ml. of carbon tetrachloride (the lower liquid phase 25) is poured into reservoir 16. Then the freshly sonicated isopropanol slurry is carefully poured down the inside of reservoir 16 so that it forms a middle liquid phase 26. The reservoir is then filled by carefully adding isooctane (the upper liquid phase 27) so that it floats above the middle phase 26. The three liquid phases, 25, 26 and 27 are referred to collectively as the "packing fluid". Reservoir 16 is then reconnected by coupling 15 to conduit 14. Valve 13 is then opened and conduits 14 and valve 13 are tapped to release any bubbles. Valve 13 is then closed and valve 7 opened. Valve 2 is opened slightly causing pump 3 to move isooctane counter-clockwise around the loop and remove any trapped air bubble. Valve 7 is then closed and pressure in conduits 5, 6 and 12 rises to 10,000 psig as shown by gauge 19. Valve 2 is then fully opened so that pump 3 is ready to give its maximum volume output to maintain 10,000 psig.

Bucket 22 is positioned below column 20 and valve 13 is quickly opened causing the liquid in reservoir 16 to be forced at about 10,000 psig. into chromatographic column 20. The liquid is discharged through end fitting 21. This is initially quite violent. After about 100 ml. of liquid has sprayed into bucket 22, valve 2 is closed inactivating the pump 3.

The silica column may be equilibriated by pumping acetone, methylene chloride and heptane through the column at 3.5 ml. per minute for 30 minutes each in succession.

The efficiency of the column is stated in plates per minute. Following the method of this invention has consistently given HPLC column having plate efficiencies of 40,000 plates per meter for 10 micron silica, 30,000 plates per meter for 10 micron $C_{18}$ reverse phase coated silica and 70,000 plates per meter for 5 micron $C_{18}$ reverse phase coated silica. Prior methods have given efficiencies of only about 20,000 plates per meter for 10 $\mu$ silica and about 15,000 plates per meter for 10 $\mu C_{18}$ reverse phase coated silica.

I claim:

1. A method for packing a high pressure liquid chromatographic column to obtain increased efficiency, said method comprising
    (a) suspending a column packing material in an alcohol medium to obtain a liquid packing suspension, said alcohol having a density similar to the density of said packing material,
    (b) forming a packing fluid comprising a lower liquid phase, a middle liquid phase and an upper liquid phase, said lower liquid phase having a density greater than said middle liquid phase, said middle liquid phase consisting of said liquid packing suspension, said upper liquid phase being an inert liquid having a density lower than said middle liquid phase and being substantially immiscible with said middle liquid phase,
    (c) rapidly injecting said packing fluid downwardly under high pressure into the inlet of an unpacked chromatographic column having an inlet and an outlet end, said column having retainer means at said outlet end which retain said packing material in said chromatographic column and permit liquids to pass through.

2. A method of claim 1 wherein said alcohol medium is isopropanol.

3. A method of claim 2 wherein said lower liquid phase is carbon tetrachloride.

4. A method of claim 3 wherein said upper liquid phase is a liquid hydrocarbon having a boiling point within the range of about 50°–200° C.

5. A method of claim 4 wherein said liquid hydrocarbon is isooctane.

6. A high efficiency high pressure liquid chromatographic column made by the method of claim 1.

* * * * *